(12) United States Patent
Uhrich et al.

(10) Patent No.: US 7,411,031 B2
(45) Date of Patent: Aug. 12, 2008

(54) SYNTHESIS OF POLYANHYDRIDES

(75) Inventors: Kathryn E. Uhrich, Plainfield, NJ (US); Robert C. Schmeltzer, Bernardsville, NJ (US); Theodore James Anastasiou, Dunellen, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 182 days.

(21) Appl. No.: 10/848,560

(22) Filed: May 18, 2004

(65) Prior Publication Data

US 2005/0131199 A1 Jun. 16, 2005

Related U.S. Application Data

(63) Continuation of application No. PCT/US02/37799, filed on Nov. 25, 2002.

(60) Provisional application No. 60/333,247, filed on Nov. 23, 2001, provisional application No. 60/333,226, filed on Nov. 23, 2001.

(51) Int. Cl.
*C08G 63/02* (2006.01)
*C07C 61/00* (2006.01)
*C07C 63/00* (2006.01)

(52) U.S. Cl. .................. 528/272; 562/400; 562/405; 562/426; 562/433; 562/565; 562/590

(58) Field of Classification Search .......... 528/274, 528/288, 289, 290, 292, 296, 299, 300, 302, 528/503, 272; 424/426; 524/186, 283; 562/400, 562/405, 426, 433, 565, 590
See application file for complete search history.

(56) References Cited

U.S. PATENT DOCUMENTS

| | | | |
|---|---|---|---|
| 3,652,502 A * | 3/1972 | Jackson, Jr. et al. ......... 528/296 |
| 4,559,157 A | 12/1985 | Smith et al. |
| 4,608,392 A | 8/1986 | Jacquet et al. |
| 4,612,302 A | 9/1986 | Szabo et al. |
| 4,684,620 A | 8/1987 | Hruby et al. |
| 4,757,128 A | 7/1988 | Domb et al. |
| 4,820,508 A | 4/1989 | Wortzman |
| 4,853,371 A | 8/1989 | Coy et al. |
| 4,857,311 A | 8/1989 | Domb et al. |
| 4,886,870 A | 12/1989 | D'Amore et al. |
| 4,888,176 A | 12/1989 | Langer et al. |
| 4,938,949 A | 7/1990 | Borch et al. |
| 4,992,478 A | 2/1991 | Geria |
| 4,997,904 A | 3/1991 | Domb |
| 4,999,417 A | 3/1991 | Domb |
| 5,235,030 A | 8/1993 | Koide |
| 5,264,540 A | 11/1993 | Cooper et al. |
| 5,902,599 A | 5/1999 | Anseth et al. |
| 6,468,519 B1 * | 10/2002 | Uhrich ..................... 424/78.01 |
| 6,486,214 B1 * | 11/2002 | Uhrich ..................... 514/772.5 |

FOREIGN PATENT DOCUMENTS

| EP | 0 463 932 | 1/1992 |
|---|---|---|
| WO | WO 99/12990 | 3/1999 |
| WO | WO 02/09767 | 2/2002 |
| WO | WO 02/09769 | 2/2002 |

OTHER PUBLICATIONS

Fessenden, Ralph J. et al, Organic Chemistry, 1982, PWS Publishers, Second Edition, p. 617.*
Allinger, Norman L. et al, Organic Chemistry, 1971, Worth Publishers, Inc., p. 528.*
International Search Report from International Application No. PCT/US02/37799, mailed Jun. 2004.
Domb et al., "Polyanhydrides. I. Preparation of High Molecular Weight Polyanhydrides", *Journal of Polymer Science: Part A: Polymer Chemistry*, 25, 3373-3386 (1987).

* cited by examiner

*Primary Examiner*—Nathan M. Nutter
(74) *Attorney, Agent, or Firm*—Viksnins Harris & Padys PLLP

(57) ABSTRACT

The present invention provides a method for forming compounds of Formula $$HO-C(=O)R^1-X-R^2-X-R^1-C(=O)-O-H$$

wherein compound (I) can be polymerized to provide a polymer that contains therapeutically active compounds. In the compounds of the invention, each $R^1$ is group that will provide the therapeutically active compound upon hydrolysis of the polymer; each X is independently an ester linkage or an amide linkage; and $R^2$ is a linking group.

26 Claims, 3 Drawing Sheets

SYNTHESIS OF POLYANHYDRIDES

CROSS-REFERENCE TO RELATED APPLICATION

This application is a continuation under 35 U.S.C. 111(a) of PCT/US02/37799, filed Nov. 25, 2002 and published in English on Jun. 5, 2003 as WO 03/046034 A2, which claims priority from U.S. Provisional Patent Application No. 60/333,247, filed: Nov. 23, 2001, and U.S. Provisional Patent Application No. 60/333,226, filed: Nov. 23, 2001, which applications and publications are incorporated herein by reference.

STATEMENT OF GOVERNMENT RIGHTS

The invention was made with the support of NIH Grant No. DE 13207. The U.S. government has certain rights in the invention.

BACKGROUND OF THE INVENTION

Polymers comprising aromatic or aliphatic anhydrides have been studied extensively over the years for a variety of uses. For example, in the 1930s fibers comprising aliphatic polyanhydrides were prepared for use in the textile industry. In the mid 1950s, aromatic polyanhydrides were prepared with improved film and fiber forming properties. More recently, attempts have been made to synthesize polyanhydrides with greater thermal and hydrolytic stability and sustained drug release properties. U.S. Pat. Nos. 4,757,128 and 4,997,904 disclose the preparation of aromatic polyanhydrides with improved sustained drug release properties from pure, isolated prepolymers of diacids and acetic anhydride. A bioerodible controlled release device produced as a homogenous polymeric matrix from polyanhydrides with aliphatic bonds having weight average molecular weights greater than 20,000 and an intrinsic velocity greater than 0.3 dL/g and a biologically active substance is also described in U.S. Pat. No. 4,888,176. Another bioerodible matrix material for controlled delivery of bioactive compounds comprising polyanhydride polymers with a uniform distribution of aliphatic and aromatic residues is disclosed in U.S. Pat. No. 4,857,311.

Biocompatible and biodegradable aromatic polyanhydrides prepared from para-substituted bis-aromatic dicarboxylic acids for use in wound closure devices are disclosed in U.S. Pat. No. 5,264,540. However, these compounds exhibit high melt and glass transition temperatures and decreased solubility, thus making them difficult to process.

Polyanhydride polymeric matrices have also been described for use in orthopedic and dental applications. For example, U.S. Pat. No. 4,886,870 discloses a bioerodible article useful for prosthesis and implantation, which comprises a biocompatible, hydrophobic polyanhydride matrix. U.S. Pat. No. 5,902,599 also discloses biodegradable polymer networks for use in a variety of dental and orthopedic applications which are formed by polymerizing anhydride or diacid prepolymers. These polymers or matrices are useful for medical applications, either with or without an active agent as part of the diacid compound.

SUMMARY OF THE INVENTION

The preparation of complex diacid precursors for preparing polyanhydride polymers reported in the art may require multiple steps, including protection and deprotection. The additional steps required to protect the acid groups prior to formation of the prepolymer can reduce the yield of the prepolymers when alternate linkages are included in the backbone e.g., esters or amides. Currently, there is a need for an efficient method that provides the diacid precursors required for preparing polyanhydride polymeric compounds, preferably compounds that contain pharmaceutically active agents. The diacid precursors can be prepared using a one-step synthesis, which provides the diacid precursors in higher yields, using fewer steps, and in greater purity (requiring minimal purification) for more complex diacid precursors.

The present invention provides an improved one-step method for forming compounds of Formula (I)

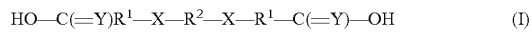  (I)

wherein each $R^1$ is an organic group; Each Y is independently O or S; each X is independently an ester linkage, an amide linkage, a thioester linkage or a thioamide linkage; and $R^2$ is an organic group; comprising reacting a compound of Formula (II)

$R^3$—$R^1$—C(=O)OH  (II)

with a compound having of Formula (III)

$X^2$—C(=Y)—$R^2$—C(=Y)—$X^2$  (III)

wherein $R^3$ is an hydroxy, amine, or thiol group or an organic radical comprising an hydroxy, amine, or thiol group; and each $X^2$ is a halogen; in the presence of at least 2 equivalents to about 50 equivalents of an organic base; optionally in a suitable solvent.

Typically, polyanhydride polymers have been prepared by the methods of Langer and Domb. (See, e.g., Domb, A.; Langer, R. Journal of Polymer Science: Part A 1987, 25, 3373-3386.) Poly(anhydride-esters) were synthesized in a similar manner, by melt condensation polymerization using prepolymer intermediates in a side-arm test tube containing a magnetic stir bar, attached to a gas-vacuum manifold. Typically, the monomers were polymerized at about 180° C. under vacuum (<2 mmHg) until the reaction mixture solidified, and the reaction vessel was flushed with dry nitrogen with stirring. Incomplete mixing, due to increased viscosity of the polymer melt as the reaction proceeded, resulted in prolonged polymerization times and low molecular weight polymers even at milligram scale. In addition, portions of the polymer melt would undergo local decomposition because of the high-localized temperatures resulting from incomplete mixing. This resulted in polymers that were dark brown in color.

The present invention also provides a method for preparing a polyanhydride polymer that comprise one or more units of Formula (IV) in the backbone

  (IV)

wherein each $R^1$ is an organic group; Each Y is independently O or S; each X is independently an ester linkage, an amide linkage, a thioester linkage or a thioamide linkage; and $R^2$ is an organic group; comprising polymerizing a compound of Formula (V):

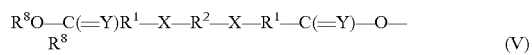  (V)

wherein each $R^8$ is a group having the formula —C(=O)($C_{1-4}$)alkyl; at a temperature of from about 40° C. to about 300° C.; and wherein the compound having Formula (V) is mechanically mixed during polymerization.

The present invention also provides a compound having Formula (IV):

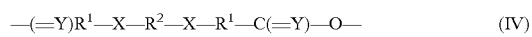  (IV)

wherein each $R^1$ is an chlorophenyl group; each X is independently an ester linkage, an amide linkage, or a thioester linkage; Each Y is independently O or S; and $R^2$ is a linking group.

The polymerization method of the invention uses di-anhydrides, having Formula (V), prepared by acylation of diacids having Formula (I). The polymers prepared using the dynamic polymerization of the invention can have an average molecular weight of about 1500 daltons to about 1,000,000 daltons, wherein $R^1$, $R^2$ and X have the same meanings as given above. The compounds that form the $R^1$ group contained within the polymer structure can have one carboxylic acid group and at least one amine, thiol, alcohol or phenol group. Thus, when $R^1$ is the residue of a therapeutic agent (drug), these polymers can function as drug delivery systems, which provide an effective means to deliver drugs in a controlled fashion as a function of polymer degradation to any site of a host.

Polyanhydride materials have been extensively studied; for example, see U.S. Pat. Nos. 4,757,128, 4,997,904, 4,888,176, 4,857,311, and 5,264,540, as well as International Patent Application Publication Numbers WO 99/12990, WO 02/09769, and WO 02/09767. Applicants have discovered that anhydride polymers having high average molecular weights possess unexpected and advantageous properties that polymers having lower average molecular weights do not possess. For example, higher molecular weight polyanhydrides typically have greater mechanical strength and higher stability. Further, higher molecular weight polyanhydrides can be made into harder and thicker coatings. Accordingly, the invention provides a polymer comprising a backbone that has a plurality of anhydride bonds, wherein the polymer has an average molecular weight of at least about 120,000 daltons.

Preferably, the polymers of the invention have an average molecular weight of at least about 130,000 daltons. Another specific polymer has an average molecular weight of at least about 140,000 daltons. Another specific polymer has an average molecular weight of at least about 150,000 daltons. Another specific polymer has an average molecular weight of at least about 175,000 daltons. Another specific polymer has an average molecular weight of at least about 200,000 daltons. Even more preferable is a polymer has an average molecular weight of at least about 300,000 daltons. Another specific polymer has an average molecular weight of at least about 500,000 daltons. Another specific polymer has an average molecular weight of at least about 600,000 daltons. Another specific polymer has an average molecular weight of at least about 750,000 daltons.

Anhydride polymers that have aryl groups in the polymer backbone have been reported in International Patent Application Publication Numbers WO 99/12990, WO 02/09769, and WO 02/09767. Applicants have discovered that anhydride polymers having high average molecular weights possess unexpected and advantageous properties that polymers having lower average molecular weights do not possess. Accordingly, the invention provides a polymer comprising a backbone that has a plurality of anhydride bonds and a plurality of aryl containing groups, wherein the polymer has an average molecular weight of at least about 40,000 daltons.

Aryl anhydride polymers that degrade (e.g. hydrolyze) to provide a therapeutic agent have been reported in International Patent Application Publication Numbers WO 99/12990, WO 02/09769, and WO 02/09767. Applicant has discovered that anhydride polymers having high average molecular weights have unexpected and advantageous properties that polymers having lower molecular weights do not possess. Accordingly, the invention provides a polymer comprising a backbone that comprises a plurality of groups of Formula (IV)

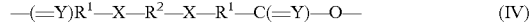
$$-(=Y)R^1-X-R^2-X-R^1-C(=Y)-O- \qquad (IV)$$

wherein each $R^1$ is independently an aryl containing group; each X is independently an amide linkage, an ester linkage, a thioamide linkage or a thioester linkage; each Y is independently O or S; and $R^2$ is a linking group; wherein the polymer has an average molecular weight of at least about 40,000 daltons.

Preferably, the aryl containing polymer has an average molecular weight of at least about 50,000 daltons. Another specific polymer has an average molecular weight of at least about 60,000 daltons. Another specific polymer has an average molecular weight of at least about 70,000 daltons. Another specific polymer has an average molecular weight of at least about 80,000 daltons. Another specific polymer has an average molecular weight of at least about 90,000 daltons. Another specific polymer has an average molecular weight of at least about 100,000 daltons. Another specific polymer has an average molecular weight of at least about 150,000 daltons. Another specific polymer has an average molecular weight of at least about 200,000 daltons. Another specific polymer has an average molecular weight of at least about 250,000 daltons.

The present invention further provides polyanhydride copolymers that comprise one or more units of Formula (IV) in the backbone wherein the repeating units having Formula (IV) can have different $R^1$ groups, different $R^2$ groups, different X groups, or any combination thereof. The invention also provides a method for preparing polyanhydride copolymers comprising polymerizing a mixture of two or more compounds of Formula (V) wherein the percentage and linkage of each repeating unit is equal to the percentage and linkage of each corresponding compound of Formula (V) and the process is carried out using dynamic polymerization at a temperature of from about 40×C to about 300×C with mechanical mixing.

The invention also provides synthetic intermediates and procedures described herein that are useful for preparing a compound of Formula (I).

DETAILED DESCRIPTION

Figure 1:
FIGS. 1 and 2 illustrate two apparatuses for dynamic melt condensation polymerization by actively stirring the molten mixture, while maintaining a high vacuum (<2 mmHg).

The present invention provides a one-step method for forming compounds of Formula (I):

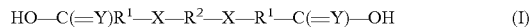
$$HO-C(=Y)R^1-X-R^2-X-R^1-C(=Y)-OH \qquad (I)$$

wherein each $R^1$ is an organic group; Each Y is independently O or S; each X is independently an ester linkage, an amide linkage, a thioester linkage or a thioamide linkage; and $R^2$ is a linking group; comprising reacting a compound of Formula (II):

$$R^3-R^1-C(=O)OH \qquad (II)$$

with a compound having of Formula (III):

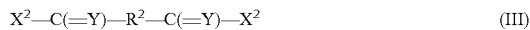

$$X^2-C(=Y)-R^2-C(=Y)-X^2 \tag{III}$$

wherein $R^3$ is an hydroxy, amine, or thiol group or an organic radical comprising an hydroxy, amine, or thiol group; and each $X^2$ is a halogen; in the presence of at least 2 equivalents to about 50 equivalents of an organic base; optionally in a suitable solvent In one embodiment, each $R^1$ is independently aryl, $(C_{1-8})$ alkylene, $(C_{2-8})$alkenylene, heteroaryl, $(C_{3-8})$cycloalkyl, or $(C_{3-8})$cycloalkenyl.

The preparation of compounds where X is a thioamide linkage can be accomplished by treating compounds of Formula (I) having amide linkages with a reagent that convert the >C(=O) group to a >C(=S) group, such as, for example, Lawesson's reagent.

The compounds of Formula (I) can be used to prepare polymers that include one or more groups in the backbone, which will yield a therapeutic agent upon breakdown of the polymer. Examples of the therapeutic agents include anti-inflammatory, analgesic, anesthetic, antipyretic anti-septic, or anti-microbial compounds. Examples of such compounds include salicylic acid, 4-aminosalicylic acid, 5-aminosalicylic acid, 4-(acetylamino)salicylic acid, 5-(acetylamino)salicylic acid, 5-chlorosalicylic acid, salicylsalicylic acid (salsalate), 4-thiosalicylic acid, 5-thiosalicylic acid, 5-(2,4-difluorophenyl)salicylic acid (diflunisal), 4-trifluoromethylsalicylic acid and the like.

In another embodiment, the compounds of Formula (I) can contain therapeutically active compounds. The compounds having Formula (II) can be therapeutically active compounds (drugs), which can be released upon hydrolysis, enzymatic cleavage, or other mechanism of breakdown of the polymer; each X is independently an ester linkage, an amide linkage, a thioester linkage or a thioamide linkage; and $R^2$ is an organic group.

The $R^2$ group is typically a divalent organic radical having a molecular weight of from about 25 daltons to about 400 daltons. More preferably, $R^2$ has a molecular weight of from about 40 daltons to about 300 daltons.

More specifically, $R^2$ is a divalent, branched or unbranched, saturated or unsaturated hydrocarbon chain, having from 1 to 25 carbon atoms, wherein one or more (e.g. 1, 2, 3, or 4) of the carbon atoms is optionally replaced by (—O—) or (—NR—), or an amino acid derivative or a peptide, and wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

The $R^3$ group is an hydroxy, amine, or thiol group or an organic radical comprising an hydroxy, amine, or thiol group. Non-limiting examples of $R^3$ groups include hydroxyalkylene, aminoalkylene or thioalkylene groups. Specific $R^3$ groups include groups such as, for example, HO$(C_{1-6})$alkylene; HS$(C_{1-6})$alkylene or $R^6$HN$(C_{1-6})$alkylene, and the like; where $R^6$ is hydrogen, $(C_1-C_6)$alkyl, $(C_3-C_6)$cycloalkyl, $(C_3-C_6)$cycloalkyl$(C_1-C_6)$alkyl, aryl or aryl$(C_1-C_6)$alkyl.

In another embodiment, the compounds having Formula (I) are formed from low molecular weight drug molecules (therapeutic agents) having Formula (VI):

wherein $R^3$ is an hydroxy, amine, or thiol group or an organic radical comprising an hydroxy, amine, or thiol group; $R^4$ is hydrogen, halo, NHR$^5$, or aryl optionally substituted with hydroxy, halo or haloC$_{1-4}$alkyl; and $R^5$ is hydrogen, $(C_{1-6})$alkyl, $(C_{3-6})$cycloalkyl, $(C_{3-6})$cycloalkyl$(C_{1-6})$alkyl, aryl, heteroaryl, aryl$(C_{1-6})$alkyl, or heteroaryl$(C_1-C_6)$alkyl or —C(O)C$_{1-4}$alkyl. Accordingly, diacids of Formula (I) are the polymer backbone of polymeric drug delivery systems comprising these low molecular weight drugs.

In one embodiment, each X is an amide linkage or each X is an ester linkage. In another embodiment, one X is an amide linkage, and one X is an ester linkage.

The Formula (II) compound contains, within its molecular structure, one carboxylic acid group. In addition, the drug contains at least one hydroxy (—OH) group, amine (—NHR$^6$) group, thiol (—SH) group, within its structure. Preferred $R^3$ groups include but are not limited to —OH, —SH, —NH$_2$, or —HNR$^6$, where $R^6$ is hydrogen, $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$alkyl, or heteroaryl$(C_1-C_6)$alkyl. $R^4$ groups include but are not limited to $(C_1-C_6)$alkyl, $(C_3-C_6)$cycloalkyl, $(C_3-C_6)$cycloalkyl$(C_1-C_6)$alkyl, aryl, heteroaryl, halo, aryl$(C_1-C_6)$alkyl, or heteroaryl$(C_1-C_6)$alkyl amino, halo$(C_1-C_6)$alkyl, (halo)aryl, and the like. Preferred $R^4$ groups are —NH$_2$, —NHAc, —Cl, 2,4-difluorophenyl, chloromethyl, difluoromethyl, —CF$_3$ and the like.

Examples of suitable biologically active compounds include salicylic acid, 4-aminosalicylic acid, 5-aminosalicylic acid, 4-(acetylamino)salicylic acid, 5-(acetylamino) salicylic acid, 5-chlorosalicylic acid, salicylsalicylic acid (salsalate), 4-thiosalicylic acid, 5-thiosalicylic acid, 5-(2,4-difluorophenyl)salicylic acid (diflunisal), 4-trifluoromethyl-salicylic acid sulfasalazine, dichlofenac, penicillamine, balsalazide, olsalazine, mefenamic acid, carbidopa, levodopa, etodolac, cefaclor, captopril, and the like.

Definitions

The following definitions are used, unless otherwise described: halogen or halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to.

As used herein an "aryl containing group" is a residue of an organic compound that has one or more aryl groups in its structure.

Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_{1-6})$alkyl, phenyl or benzyl, as well as a radical of an ortho-fused bicyclic heterocycle of about eight to ten ring atoms derived therefrom, particularly an aryl-derivative or one derived by fusing a propylene, trimethylene, or tetramethylene diradical thereto.

The term ester linkage means —OC(=O)— or —C(=O)O—; the term amide linkage means —N(R)C(=O)— or —C(=O)N(R)—; the term thioester linkage means —SC(=O)— or —C(=O)S—; and the term thioamide linkage means —N(R)C(=S)— or —C(=S)N(R)—, wherein each R is a suitable organic radical, such as, for example, hydrogen, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$alkyl, or heteroaryl$(C_1-C_6)$alkyl.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a $(C_1-C_6)$alkyl, phenyl or benzyl ester or amide; or as an α-methylbenzyl amide). Other suitable amino and carboxy protecting groups are known to those skilled in the art (See for example, Greene, T. W.; Wutz, P. G. M. "Protecting Groups In Organic Synthesis" second edition, 1991, New York, John Wiley & sons, Inc., and references cited therein).

The term "peptide" describes a sequence of 2 to 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20 amino acids, or preferably 5 to 15 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

The term "therapeutic agent" includes any compound that provides a beneficial therapeutic effect when administered to a mammal. The term includes anti-inflammatory, analgesic, anesthetic, antipyretic anti-septic, or anti-microbial compounds.

The term "dynamic polymerization or mechanical mixing" refers to a method for polymerizing the compounds having Formula (I) wherein the polymerization apparatus can actively stir the molten polymerization mixture. This will minimize the discoloration due to incomplete mixing of the polymerization mixture.

The invention provides a general method that is useful for preparing a wide array of diacid compounds that are useful, for example, for preparing polyanhydrides. Accordingly, the nature of the "organic group" $R^1$ is not critical provided it is a group that does not interfere with the synthetic method of the invention. The organic group can be any organic compound that contains one or more carbon atoms. In one embodiment, the organic group includes from one to one hundred carbon atoms; the organic group can also include a number of heteroatoms and/or functional groups, as well as mono- di- and poly-cyclic rings, and aromatic and heteroaromatic rings. In another embodiment, the organic group includes from one to fifty carbon atoms. In another embodiment, the organic group includes from one to twenty carbon atoms. Typically, the organic group has a molecular weight of less than about 500 amu. In one embodiment, the organic group has a molecular weight of less than about 300 amu. In another embodiment, the organic group has a molecular weight of less than about 200 amu. In one embodiment, the method of the invention is useful for preparing diacid intermediates that are useful for preparing anhydride polymers that have therapeutic agents in the polymer backbone; accordingly, the "organic group" $R^1$ can be the residue of a therapeutic agent.

Diacid Synthesis

A representative general synthesis for preparing the compounds of Formula (I) is illustrated in Scheme 1. A free (unprotected) salicylate (6) can be directly coupled with the diacyl halide (7) in the presence of at least about 2 equivalents to about 50 equivalents of an organic base such as, for example, pyridine and the like in a suitable solvent, such as, for example, tetrahydrofuran (THF), dimethyl formamide (DMF) or mixtures thereof, to provide the compounds of Formula (I). In one embodiment, the process uses solvents such as tetrahydrofuran (THF) and N,N-dimethyl formamide (DMF), in the presence of stoichiometric pyridine. In another embodiment, there is an excess of pyridine or the pyridine is used as a co-solvent, e.g., 3 parts THF to 1 part pyridine, by volume). In another embodiment, there is no solvent other than the organic base.

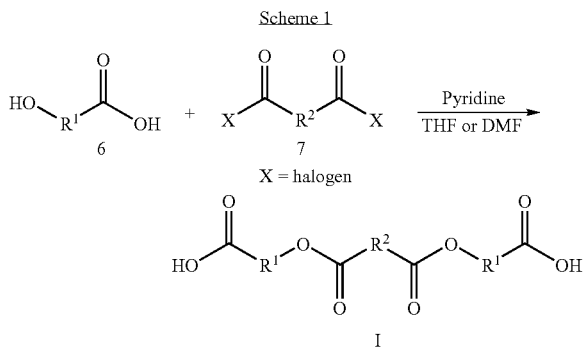

Scheme 1

The present method eliminates the need to protect the acid groups of the salicylates, 6. In addition, there is no need for further purification of the diacid product (I), except for washing with an appropriate suitable solvent. This is because of the large differences in solubility between the products (I) and any by-products that can be formed. The solvent choice is dependent upon the solubility characteristics of the salicylate used. Resultant conversions are quantitative and isolated yields are greater than 80%.

Polymerization.

The biocompatible, biodegradable polyanhydride polymers prepared by the process of the invention may be used to produce a variety of useful products with valuable physical and chemical properties. The polyanhydride polymers are useful in applications, such as, for example, the delivery of biologically active compounds, preparing films, coatings, medical implants, coatings for medical implants and the like.

The polymers prepared by the process of the invention can be readily processed into pastes or films, coatings, microspheres and fibers with different geometric shapes for design of various medical implants. The polymers can be processed into finished articles or coatings using techniques known in the art, such as, for example, solvent casting, spraying solutions or suspensions, compression molding and extrusion. Examples of such applications include, but are not limited to, medical, dental and cosmetic uses.

Medical implant applications include the use of the polyanhydrides to form shaped articles such as vascular grafts and stents, bone plates, sutures, implantable sensors, implantable drug delivery devices, stents for tissue regeneration, and other articles that decompose into non-toxic components within a known time period. In addition, the polymers can be used to form coating layers for articles such as vascular grafts and stents, bone plates, sutures, implantable sensors, implantable drug delivery devices, stents for tissue regeneration, and other articles, which may require the release of an active compound.

Polymers prepared from the process of the present invention can also be incorporated into oral formulations and into products such as skin moisturizers, cleansers, pads, plasters, lotions, creams, gels, ointments, solutions, shampoos, tanning products and lipsticks for topical application.

Although the invention provides a process to prepare polymers that are prepared from suitably functionalized compounds having Formula (I), the mechanical and degradation properties of polymers comprising one or more compounds having Formula (II) can be controlled by modifying the linking group ($R^2$) in the polymer backbone. The polymers prepared from the compounds having Formula (I) can be homopolymers, i.e., having identical repeating units having Formula (IV), or copolymers, i.e., having two or more repeating units having Formula (IV) where the repeating units having Formula (IV) have different $R^1$ groups, different $R^2$ groups, different X groups or any combination thereof.

Preferably, the polymers prepared from the process of the present invention comprise backbones wherein biologically active compounds and linker groups ($R^2$) are bonded together through ester linkages, thioester linkages, amide linkages, thioamide linkages, or a mixture thereof. Due to the presence of the ester, thioester, amide, and/or thioamide linkages, the polymers can be hydrolyzed, enzymatically, or otherwise degraded under physiological conditions to provide the biologically active compounds. Thus, the polymers prepared from the process of the present invention can be particularly useful as a controlled release source for a biologically active compound, or as a medium for the localized delivery of a biologically active compound to a selected site. For example, the polymers prepared from the process of the present invention can be used for the localized delivery of a therapeutic agent to a selected site within the body of a human patient (i.e. within or near a tumor), where the degradation of the polymer provides localized, controlled, release of the therapeutic agent.

The polyanhydrides prepared using the dynamic polymerization of the invention can have an average molecular weight of about 1500 daltons to about 1,000,000 daltons. Preferred aromatic polyanhydrides have average molecular weights of about 10,000 daltons, up to about 200,000 daltons. The average molecular weight ($M_w$) is determined using Gel Permeation Chromatography (GPC) relative to narrow molecular weight polystyrene standards.

In another embodiment, the polymers prepared using the dynamic polymerization of the invention can have an average molecular weight between about 1500 daltons up to about 100,000 daltons.

Polymers

The polymerization apparatuses illustrated in the figures provided herein are designed to facilitate the dynamic polymerization and provide higher molecular weight materials on both the milligram and gram scale. However, the polymerization can be carried out using any mechanical mixing equipment or method known in the art. Examples of equipment and methods suitable for preparing polymers according to the process of the invention include a plow-type mixer, screw-type extruder, ribbon-type mixer, reciprocating venturi turn-screw mixer extruder, extruder with inline static mixer, Banbury mixer conical screw blender, compound helical mixer, open-helical blade mixer, auger-type mixer, anchor-type blade mixer, multi-shaft mixer, and the like.

One embodiment of the dynamic polymerization process for preparing polyanhydride polymers from the diacid/precursors having Formula (I) is provided as a further embodiment of the invention. An illustrative process is presented in Scheme II, in which the meanings of the generic radicals are as given above unless otherwise qualified. For example, a polyanhydride polymer can be prepared by the process of the present invention, as illustrated in Scheme II, from a precursor having Formula (I). Diacid/precursor, Ia, is acylated using acetic anhydride. (See, for example, Conix, Macromol. Synth., 2, 95-99 (1996).) After removal of acetic acid or acetic anhydride, the acetylated compound, Ib, is stirred and heated at a temperature of from about 40° C. to about 300° C., under vacuum to effect polymerization and remove acetic acid. Preferably, the polymerization mixture is heated at a temperature of from about 100° C. to about 220° C. More preferably the polymerization temperature is from about 100° C. to about 180° C. The monomer mixture is mechanically agitated during polymerization. Typically, the polymerization mixture is stirred at a speed of from about 40 revolutions per minute (rpm) to about 200 rpm and preferably from about 50 rpm to about 150 rpm. This provides the anhydride polymer, IIa.

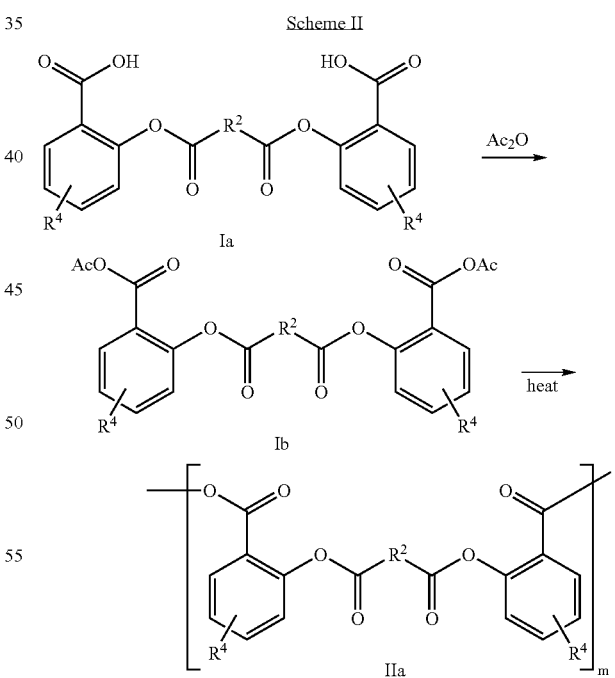

A second embodiment of the dynamic polymerization process includes the isolation and purification of the intermediate precursor/prepolymer Ib in Scheme II. For example, the diacid/precursor Ia (Scheme II) is acetylated using acetic anhydride as described above. In this embodiment, a portion but not all of the acetic acid or acetic anhydride is removed by distillation. The prepolymer Ib is induced to crystallize from solution by the addition of an appropriate solvent. For example, in the preparation of Ib 50 to 80% of acetic acid or acetic anhydride is removed by distillation and the prepolymer is made to crystallize by way of the addition of a mixture of ethyl ether and petroleum ether. In this embodiment, the purified prepolymer Ib is isolated and polymerized in a separate operation. For example, purified Ib (Scheme II) is isolated by filtration and vacuum drying, and then is mechanically agitated and heated at a temperature from about 40° C. to about 300° C. under vacuum to effect polymerization and remove acetic anhydride. The prepolymer is mechanically agitated during polymerization. Typically, the polymerization mixture is stirred at a speed of from about 40 rpm to 200 rpm and preferably from about 50 rpm to 150 rpm. This provides the anhydride polymer.

Figure 2:
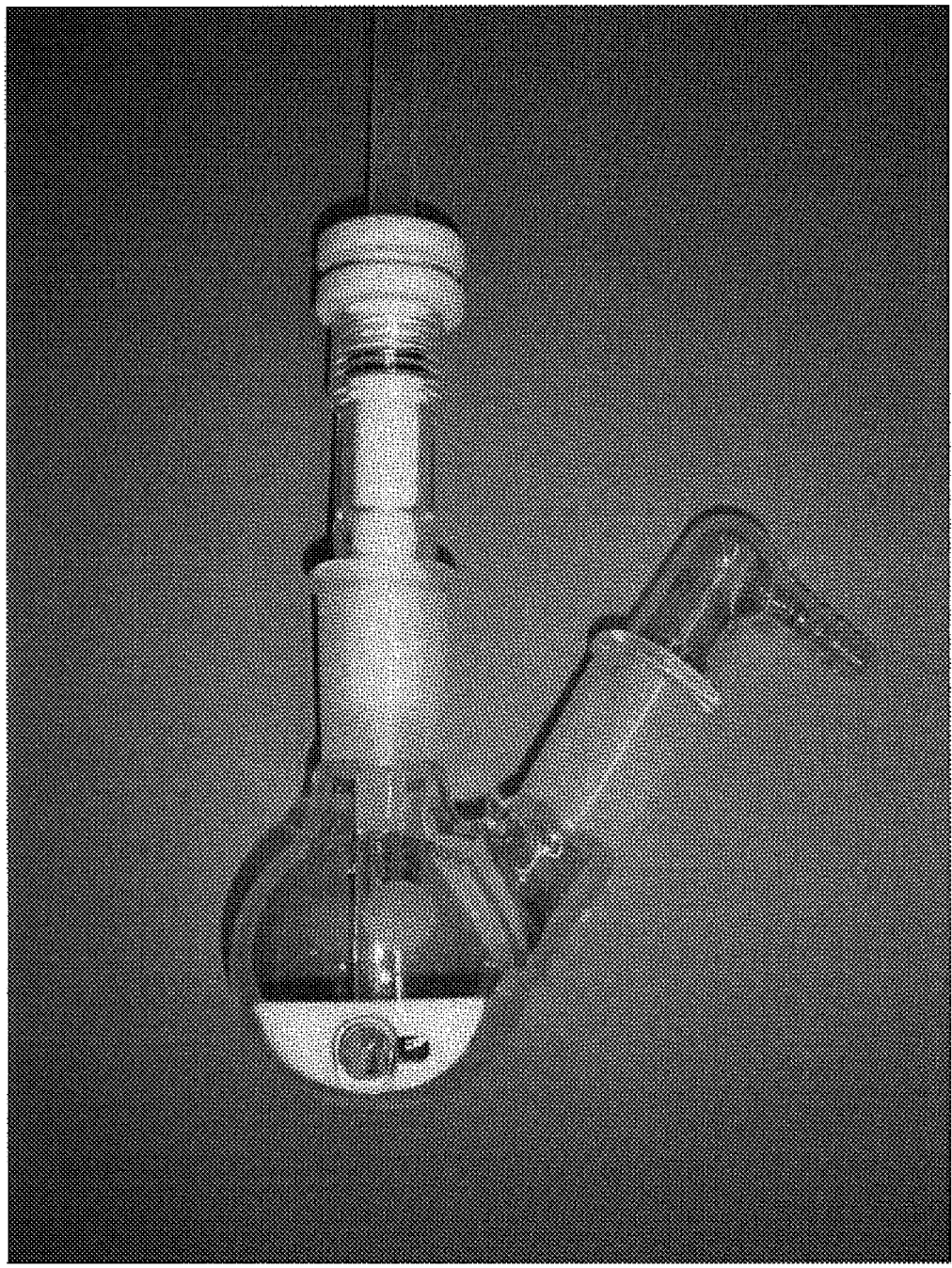

By altering the polymerization using simple, inexpensive, and readily available components, a polymerization apparatus that actively stirred the molten polymerization mixture, while maintaining a high vacuum (<2 mmHg) was constructed. Both small (<1 g) and medium (1 g-100 g) scale polymerizations can be performed using a typical laboratory stirring motor. Examples of polymerization vessels suitable for dynamic mixing with a mechanical stirrer are illustrated in FIGS. 1 and 2, as a function of batch size. The dynamic mixing of the present invention provides polymers with increased molecular weights.

In another embodiment of the invention a polymerization process for preparing polyanhydride copolymers from a mixture of polymer precursors of Formula (V) wherein the precursors have different $R^1$ groups, different $R^2$ groups, different X groups, or any combination thereof is provided. For example, a polyanhydride copolymer can be prepared by the process of the present invention from a mixture of precursors having the Formula (V). In each precursor at least one of the $R^1$ groups, $R^2$ groups, or X groups is different than the corresponding group in the second precursor, e.g., two R1 groups in two different precursors can provide different therapeutic agents upon degradation.

Therapeutically Active Agents

It has been found that the polyanhydride compounds of the invention can serve as a polymer backbone for degradable polymeric drug delivery systems for a multitude of low molecular weight therapeutically active agents (drugs), such as, for example, those disclosed in U.S. Pat. No. 6,486,214. Drugs, which can be linked into degradable co-polymers via the polyanhydrides, have the following characteristics. The drugs preferably have relatively low molecular weights of approximately 1,000 daltons or less. The drugs contain within its molecular structure at least one carboxylic acid group. In addition, the drugs contain at least one hydroxy (—OH), amine (—$NHR^6$), or thiol (—SH), group within its structure.

In another embodiment, each $R^1$ is derived from a compound having the Formula (VI):

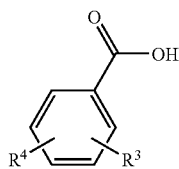

wherein $R^3$ is an amine, thiol, or hydroxy group; $R^4$ is hydrogen, halo, $NHR^5$, or aryl optionally substituted with hydroxy, halo or halo$C_{1-4}$alkyl; and $R^5$ is hydrogen, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$alkyl, or heteroaryl$(C_1-C_6)$alkyl or —$C(O)C_{1-4}$alkyl.

In another embodiment each $R^1$ is an aryl containing group that will yield a therapeutic agent upon hydrolysis of the polymer.

In another embodiment each therapeutic agent is independently an anti-inflammatory, analgesic, anesthetic, or antipyretic compound comprising a carboxylic acid group and at least one amine, thiol, or hydroxy group.

Linking Group "$R^2$"

The nature of the linking group "$R^2$" in a polymer of the invention is not critical provided the polymer of the invention possesses acceptable mechanical properties and release kinetics for the selected therapeutic application. The linking group $R^2$ is typically a divalent organic radical having a molecular weight of from about 25 daltons to about 400 daltons. More preferably, $R^2$ has a molecular weight of from about 40 daltons to about 300 daltons.

The linking group $R^2$ typically has a length of from about 5 angstroms to about 100 angstroms using standard bond lengths and angles. More preferably, the linking group L has a length of from about 10 angstroms to about 50 angstroms.

The linking group may be biologically inactive, or may itself possess biological activity. The linking group can also comprise other functional groups (including hydroxy groups, mercapto groups, amine groups, carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

Specific and Preferred Values

Specific and preferred values listed herein for radicals, substituents, groups, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^2$ is a divalent, branched or unbranched, saturated, or unsaturated hydrocarbon chain, having from 1 to 25 carbon atoms, wherein one or more (e.g. 1, 2, 3, or 4) of the carbon atoms is optionally replaced by (—O—) or (—NR—), or an amino acid derivative or a peptide, and wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_{12})$alkanoyl, $(C_1-C_6)$alkanoyloxy, $(C_1-C_6)$alkoxycarbonyl, $(C_1-C_6)$alkylthio, —OP(=O)O$(C_1-C_{12})$alkyl, azido, cyano, nitro, halo, hydroxy, oxo, carboxy, aryl, aryloxy, heteroaryl, and heteroaryloxy.

$R^2$ is a divalent, branched or unbranched, saturated or unsaturated hydrocarbon chain, having from 1 to 20 carbon atoms, wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

Another specific value for $R^2$ is —(CHR$^9$)$_4$— where each R9 is hydrogen, —C(=O)(CH$_2$)$_{10}$CH$_3$ or —OP(=O)O(CH$_2$)$_{10}$CH$_3$.

Another specific value for $R^2$ is an amino acid.

Another specific value for $R^2$ is a peptide.

Another specific value for $R^2$ is a divalent, branched or unbranched, saturated or unsaturated hydrocarbon chain, having from 1 to 20 carbon atoms, wherein one or more (e.g. 1, 2, 3, or 4) of the carbon atoms is optionally replaced by (—O—) or (—NR—).

A more specific value for $R^2$ is a divalent, branched or unbranched, saturated or unsaturated hydrocarbon chain, having from 3 to 20 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

Another more specific value for $R^2$ is a divalent, branched or unbranched, saturated or unsaturated hydrocarbon chain, having from 3 to 20 carbon atoms, wherein one or more (e.g. 1, 2, 3, or 4) of the carbon atoms is optionally replaced by (—O—), (—C(O)O—), (—C(S)O—), (—C(O)NR$^7$—), (—C(S)NR$^7$—), or (—NR$^7$—), wherein R$^7$ is hydrogen or $(C_1-C_6)$alkyl.

Another more specific value for $R^2$ is a divalent, branched or unbranched, saturated or unsaturated hydrocarbon chain, having from 3 to 20 carbon atoms.

A preferred value for $R^2$ is a divalent, branched or unbranched, hydrocarbon chain, having from 4 to 15 carbon atoms.

Specific divalent hydrocarbon chains are n-butyl, n-hexyl, n-octyl, n-decyl, n-dodecyl or n-tetradecyl.

Another preferred value for $R^2$ is a divalent hydrocarbon chain having 8 or 14 carbon atoms.

A specific value for $R^3$ group is HO$(C_{1-6})$alkylene; HS$(C_{1-6})$alkylene or R$^6$HN$(C_{1-6})$alkylene.

Another specific value for $R^3$ is —OH, —SH, —NH$_2$, or —HNR$^6$.

A more specific value for $R^3$ is —OH, —SH, or —NH$_2$.

A specific value for $R^4$ is halo, NHR$^5$, or aryl optionally substituted with hydroxy, halo or haloC$_{1-4}$alkyl; and R$^5$ is hydrogen or —C(O)C$_{1-4}$alkyl.

Another specific value for $R^4$ is —NH$_2$, —NHAc, —Cl, 2,4-difluorophenyl, chloromethyl, difluoromethyl, —CF$_3$.

Another specific value for $R^4$ is —Cl, or 2,4-difluorophenyl,

A specific value for $R^5$ is hydrogen or $(C_1-C_6)$alkyl.

A specific value for $R^5$ is hydrogen, methyl, ethyl or propyl.

A specific value for $R^6$ is hydrogen, $(C_1-C_6)$alkyl, $(C_3-C_6)$cycloalkyl, $(C_3-C_6)$cycloalkyl$(C_1-C_6)$alkyl, aryl or aryl$(C_1-C_6)$alkyl.

A specific value for $R^7$ is hydrogen, methyl, ethyl or propyl.

A specific value for $R^8$ is a —C(=O)CH$_3$.

A specific value for Y is O.

A specific polyanhydride polymer of the present invention includes biologically active compounds provided that the biologically active compound is a hydroxy carboxylic acid.

A specific polyanhydride polymer of the present invention includes biologically active compounds provided that the biologically active compound is an alpha-hydroxy carboxylic acid.

A specific polyanhydride polymer of the present invention includes biologically active compounds provided that the biologically active compound is a hydroxy aryl carboxylic acid.

A specific polyanhydride polymer of the present invention includes biologically active compounds provided that the biologically active compound is an ortho-hydroxy aryl carboxylic acid.

Another specific polyanhydride polymer is a polymer where salicylic acid is the biologically active compound and $R^2$ is —(CH$_2$)$_8$—.

Another specific polyanhydride polymer is a polymer where diflunisal is the biologically active compound and $R^2$ is —(CH$_2$)$_{14}$—.

Such a polymer, wherein each R is a group that will provide a different biologically active compound upon hydrolysis of the polymer, are particularly useful for the administration of a combination of two therapeutic agents to an animal or a plant.

Formulations

The polymers of the invention can be formulated as pharmaceutical compositions and administered to a mammalian host, such as a human patient in a variety of forms adapted to the chosen route of administration, i.e., orally, rectally, or parenterally, by intravenous, intramuscular, intraperitoneal, intraspinal, intracranial, topical, ocular or subcutaneous routes. For some routes of administration, the polymer can conveniently be formulated as micronized particles.

Thus, the present polymeric compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations preferably contain at least 0.1% of polymer by weight. The percentage of the compositions and preparations may, of course, be varied and may conveniently be between about 2 to about 80% of the weight and preferably 2 to about 60% of a given unit dosage form. The amount of polymer in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polymeric compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The polymer may also be administered intravenously, intraspinal, intracranial, or intraperitoneally by infusion or injection. Solutions of the polymer can be prepared in a suitable solvent such as an alcohol, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms The pharmaceutical dosage forms suitable for injection or infusion can include sterile solutions or dispersions or sterile powders comprising the polymer containing the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

For topical administration, the present polymers can be applied in pure form. However, it will generally be desirable to administer them as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include, alcohols or glycols or alcohol/glycol blends, in which the present compounds can be dissolved or dispersed at effective levels, optionally with the aid of non-toxic surfactants. Adjuvants such as fragrances and additional anti-microbial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the polymers of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Dosages

Useful dosages of the polymers can be determined by comparing their in vitro activity, and in vivo activity of the therapeutic agent in animal models. Methods for the extrapolation of effective dosages in mice, and other animals, to humans are known to the art; for example, see U.S. Pat. No. 4,938,949. Additionally, useful dosages can be determined by measuring the rate of hydrolysis for a given polymer under various physiological conditions. The amount of a polymer required for use in treatment will vary not only with the particular polymer selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Combination Therapies

The polymers of the invention are also useful for administering a combination of therapeutic agents to an animal. Such a combination therapy can be carried out in the following ways: 1) a second therapeutic agent can be dispersed within the polymer matrix of a polymer of the invention, and can be released upon degradation of the polymer; 2) a second therapeutic agent can be appended to a polymer of the invention (i.e., as a sidechain on the polymer) with bonds that hydrolyze to release the second therapeutic agent under physiological conditions; 3) the polymer of the invention can incorporate two therapeutic agents into the polymer backbone (e.g. a polymer comprising one or more units of Formula (I)) or 4) two polymers of the invention, each with a different therapeutic agent can be administered together (or within a short period of time).

Thus, the invention also provides a pharmaceutical composition comprising a polymer of the invention and a second therapeutic agent that is dispersed within the polymer matrix of a polymer of the invention. The invention also provides a pharmaceutical composition comprising a polymer of the invention having a second therapeutic agent appended to the polymer (e.g. with bonds that will hydrolyze to release the second therapeutic agent under physiological conditions).

The polymers of the invention can also be administered in combination with other therapeutic agents that are effective to treat a given condition to provide a combination therapy. Thus, the invention also provides a method for treating a disease in a mammal comprising administering an effective amount of a combination of a polymer of the invention and another therapeutic agent. The invention also provides a pharmaceutical composition comprising a polymer of the invention, another therapeutic agent, and a pharmaceutically acceptable carrier.

The invention will now be illustrated by the following non-limiting Examples

EXAMPLES

Materials. Solvents and reagents were purchased from Fisher (Pittsburgh, Pa.), and fine chemicals from Aldrich (St. Louis, Mo.). All reagents were used as received. Polymerization glassware was obtained from Kimble-Kontes (14/10 microscale glassware) and ChemGlass (24/40 glassware) and used without modification. Stainless steel lab spoons (Spoonula) were obtained from Fisher and were modified using a machine-shop grinder.

Methods. Proton nuclear magnetic resonance ($^1$H-NMR) were recorded on either a Varian 200 MHz or 300 MHz spectrometer. Samples (5-10 mg) were dissolved in the appropriate deuterated solvent, with the solvent as the internal reference. Infrared (IR) spectra were measured on a Mattson Series spectrophotometer by solvent-casting samples onto a sodium chloride plate. Melting points ($T_m$) were determined on a Thomas-Hoover apparatus.

Molecular weights ($M_w$) and polydispersity indices (PDI) were determined by gel permeation chromatography (GPC) on a Perkin-Elmer (PE) LC system consisting of a Series 200 refractive index detector, a Series 200 pump, and an ISS 200 autosampler. A DEC Celebris 466 computer running PE TurboChrom 4 software was used for data collection and processing, and to automate the analysis via PE-Nelson 900 Interface and 600 Link. Samples (5 mg/ml) were dissolved in THF and filtered through 0.45 μm poly(tetrafluoroethylene) (PTFE) syringe filters (Whatman Inc., Clifton, N.J.). Samples were resolved on a Jordi DVB mixed-bed GPC column (7.8× 300 mm) (Alltech Associates, Inc., Deerfield, Ill.). Molecular weights were calibrated relative to narrow molecular weight polystyrene standards (Polysciences, Dorval, Canada).

Example 1

1,10-Bis-salicylic-sebacate

Salicylic acid (1.2 g, 8.4 mmol) was dissolved in THF (3.0 ml) containing pyridine (9.0 ml). Sebacoyl chloride (1.0 g, 4.2 mmol) was added dropwise via syringe over 5 minutes with stirring in an ice bath (~0° C.). The reaction was allowed to come to room temperature, stirred for 2 hours, then poured over an ice/water slush (150 ml). After acidifying to pH~2 with concentrated HCl, the product was isolated by vacuum filtration, purified by washing with water (3×50 ml), and air-dried. Yield: 91% (white powder).

$^1$H-NMR (CDCl$_3$): δ 8.13 (d, 2H, ArH), 7.61 (t, 2H, ArH), 7.35 (t, 2H, ArH), 7.12 (d, 2H, ArH), 2.63 (t, 4H, CH$_2$), 1.82 (m, 4H, CH$_2$), 1.48 (b, 8H, CH$_2$). IR (NaCl, cm$^{-1}$): 3400-2700 (COOH), 1760 (C=O, ester), 1700 (C=O, ester). Anal. Calcd: C, 65.18; H, 5.88. Found: C, 64.50; H, 5.73. $T_m$=128-131° C.

Example 2

1,10-Bis-4-acetamidosalicyl-sebacate

4-Acetamidosalicylic acid (2.2 g, 11 mmol) was dissolved in ice-cold N,N-dimethylformamide (DMF) (50 ml) containing pyridine (20 ml). Sebacoyl chloride (0.90 g, 3.8 mmol) in DMF (1.0 ml) was added dropwise via syringe over 5 minutes with stirring. The reaction was maintained at ~0° C. by an ice bath. After 6 hours, the mixture was poured over an ice/water slush (200 ml) and acidified to pH~2 with concentrated HCl. The precipitated product was isolated by vacuum filtration, washed with water (2×50 ml), and air-dried. Yield: 98% (white powder).

$^1$H-NMR (DMSO-d$_6$): δ 10.22 (s, 2H, ArNH), 7.82 (d, 2H, ArH), 7.50 (s, 2H, ArH), 7.38 (d, 2H, ArH), 2.40 (t, 4H, CH$_2$), 2.02 (s, 6H, CH$_3$), 1.60 (m, 4H, CH$_2$), 1.30 (b, 8H, CH$_2$). IR (NaCl, cm$^{-1}$): 3400-2750 (COOH), 3340 (N—H), 1765 (C=O, ester), 1700 (C=O, ester), 1680 (C=O, amide I), 1620 (NH, amide II). Anal. Calcd: C, 60.43; H, 5.76; N, 5.04. Found: C, 59.56; H, 5.76; N, 4.81. $T_m$=184-186° C.

Example 3

1,10-Bis-5-acetamidosalicyl-sebacate

5-Acetamidosalicylic acid (12.2 g, 62.7 mmol) was dissolved in ice-cold THF (500 ml) containing pyridine (17.8 ml, 209 mmol). Sebacoyl chloride (5.00 g, 20.9 mmol) dissolved in THF (7.0 ml) was added dropwise via addition funnel over 10 min. with stirring in an ice bath (~0° C.). After stirring for 6 hours at ~0° C., the reaction was poured into an ice/water slush (400 ml) and acidified to pH~2 with concentrated HCl. The precipitated product was isolated by vacuum filtration. The residue was washed with 30% ethanol (4×100 ml), and air-dried to provide the title product. Yield: 96% (white crystals).

$^1$H-NMR (DMSO-d$_6$): δ 10.15 (s, 2H, ArNH), 8.15 (s, 2H, ArH), 7.82 (d, 2H, ArH), 7.12 (d, 2H, ArH), 2.58 (t, 4H, CH$_2$), 2.08 (s, 6H, CH$_3$), 1.65 (m, 4H, CH$_2$), 1.38 (b, 8H, CH$_2$). IR (NaCl, cm$^{-1}$): 3400-2600 (COOH), 3370 (NH), 1710 (C=O, ester), 1700 (C=O, ester), 1650 (C=O, amide I), 1610 (NH, amide II). Anal. Calcd: C, 60.43: H, 5.76; N, 5.04. Found: C, 60.34; H, 5.84; N, 4.72. $T_m$=205-206° C.

Example 4

1,10-Bis-4-chlorosalicyl-sebacate

Pyridine (9 mL, 0.111 mol) was added to a mixture of 5-chlorosalicylic acid (1.44 g, 0.008 mol) and THF (3 mL, 0.037 mol). The reaction mixture was stirred thoroughly before sebacoyl chloride (1 g, 0.004 mol) was added dropwise. The mixture was stirred for 2 hours, poured over an ice/water bath, acidified to pH=2 by addition of concentrated HCl (aq.), filtered, and washed with water to yield a white solid. Yield 95%. The melting point range was 176-181° C.

Infrared absorption frequencies were 1753, 1687 and 1098 cm$^{-1}$. NMR chemical shifts (DMSO, ppm) δ 7.9 (s, Ar H, 2 H), 7.7 (d, Ar H, 2 H), 7.25 (d, Ar H, 2 H), 2.55 (t, α-CH$_2$, 4 H), 1.6 (p, β-CH$_2$, 4 H), and 1.35 (m, γ-CH$_2$, 4 H).

Example 5

1,10-Bis-5-(2,4-difluorophenyl)salicyl-sebacate

Pyridine (0.8 mL, 0.010 mol) was added to a mixture of diflunisal (1.16 g, 0.008 mol) and THF (25 mL, 0.308 mol). The mixture was then cooled to 0° C. by an ice/water bath. Next, the reaction mixture was stirred thoroughly and sebacoyl chloride (1 g, 0.004 mol)/THF (10 mL, 0.123 mol) mixture was added dropwise. The mixture was stirred for 2 hours at 0° C., poured over an ice/water bath, acidified to pH=2 by addition of concentrated HCl (aq.), filtered, and washed with water to yield a white solid. Yield 96%. The melting point range was 162-165° C.

Infrared absorption frequencies were 1754, 1658, 1139 and 1104 cm$^{-1}$. NMR chemical shifts (CDCl$_3$, ppm) δ 8.25 (s, Ar H, 2 H), 7.65 (dd, Ar H, 2 H), 7.4 (td, Ar H, 2 H), 7.2 (d, Ar H, 2 H), 6.95 (m, Ar H, 4H), 2.65 (t, α-CH$_2$, 4 H), 1.8 (p, β-CH$_2$, 4 H), and 1.45 (m, γ-CH$_2$, 4 H).

Example 6

1,10-Bis-Salicylsalicyl-sebacate (SSA)

NaH (0.5 g, 0.021 mol) was added to a mixture of salicyl-salicylic acid (1.03 g, 0.004 mol) and THF (25 mL, 0.308 mol). The reaction mixture was cooled to 0° C. with an ice/water bath. The reaction mixture was stirred and sebacoyl chloride (0.5 g, 0.002 mol)/THF (5 mL, 0.062 mol) mixture was added dropwise. The mixture was stirred for 2 hours at 0° C., poured over an ice/water bath, acidified to pH=2 by addition of concentrated HCl (aq.), filtered, and washed with water to yield a white solid. Yield 83%. The melting point range was 142-148° C.

Infrared absorption frequencies were 1751 and 1662 cm$^{-1}$. NMR chemical shifts (CDCl$_3$, ppm) $\delta$ 8.2 (dd, Ar H, 4H), 7.6 (t, Ar H, 4 H), 7.45 (dt, Ar H, 4 H), 7.15 (t, Ar H, 4 H), 2.5 (t, $\alpha$-CH$_2$, 4 H), 1.8 (p, $\beta$-CH$_2$, 4 H), and 1.35 (m, $\gamma$-CH$_2$, 4 H).

Example 7

1,14-Bis-5-(2,4-difluorophenyl)salicyl tetradecandioate

Pyridine (70. Ml, 865 mmol) was added to a solution of diflunisal (71.06 g, 284 mmol) in THF (800 ml). The solution was cooled to 0° C. by an ice/water bath. Next, the reaction was stirred thoroughly and a solution of tetradecanedioyl dichloride (41.6 g, 141 mmol) in THF (130 ml) was added dropwise. The mixture was stirred for 1 hour at room temperature, poured over an ice/water/HCl mixture (final pH 2), filtered, and washed with water to yield a white solid. Yield 96%. The melting point range was 150-151° C.

$^1$H-NMR chemical shifts (CDCl$_3$, ppm) $\delta$ 8.01 (m, 2H), 7.79 (m, 2H), 7.63 (m, 2H), 7.37 (m, 2H), 7.27 (m, 2H), 7.19 (m, 2H), 2.48 (m, 4H), 1.62 (m, 4H), 1.22 (m, 16H).

Example 8

1,14-Bis-5-(2,4-difluorophenyl)salicyl tetradecandioate mixed acetic acid anhydride A suspension of 1,14-Bis-5-(2,4-difluorophenyl)salicyl tetradecandioate from Example 7 (70.0 g) in acetic anhydride (700 mL) was layered with dry argon and stirred in a bath maintained at 65-70° C. for 1-2 hours. Acetic anhydride was distilled from the resulting clear homogeneous solution at 65-70° C. under reduced pressure. After about 600 ml of acetic anhydride was collected in a chilled receiver (−78° C.), a white solid began to separate from the reaction mixture. The distillation was terminated; the reaction mixture was blanketed with dry argon and placed in an ice bath. Then 300 ml of 1 ethyl ether: 1 petroleum ether was added, and the slurry was stirred for 0.5-2 h at ice-bath temperature. The slurry was then sealed under an atmosphere of argon and incubated at −20° C. for 16-40 hours. The product was collected by filtration and washed with ice-cold ethyl ether (50 ml). The filtration and washing steps were conducted under reduced pressure with a dynamic blanket of dry argon provided by a rapid stream of argon delivered via an inverted stem funnel suspended over the product contained in a Buchner funnel (Note 5). The product was thus dried under a stream of argon for 0.5-1 hours, then placed under vacuum at room temperature for 4-16 hours. Yield: 71 g (90.9%).

Melting point range 100-101° C. 1H NMR (CDCl3): $\delta$ 8.09 (m, 2H), 7.58 (m, 2H), 7.40 (m, 2H), 7.24 (m, 2H), 6.96 (m, 4H), 2.62 (m, 4H), 2.39 (s, 6H), 1.79 (m, 4H), 1.35 (m, 16H).

The yields of the product diacids prepared using the methods known in the art and the one-step method of the invention are summarized in Table 1, below. The one-step synthesis provides the diacid precursors at higher yields and with increased purity that the methods disclosed in the art.

TABLE 1

| | | Old Synthesis | | One-Step Synthesis | |
|---|---|---|---|---|---|
| Ex # | Active Agent[1] | No. Steps | Yield(%) | No. Steps | Yield(%) |
| 1 | SA | 2 | 83% | 1 | 91% |
| 2 | 4-ASA | 4 | 31% | 1 | 98% |
| 3 | 5-ASA | 4 | 29% | 1 | 96% |
| 4 | 5-Cl-SA | — | — | 1 | 95% |
| 5 | 5-F$_x$-SA | — | — | 1 | 96% |
| 6 | SSA | — | — | 1 | 83% |

[1]SA = Salicylic acid; 5-ASA = 5-Acetamidosalicylic acid; 4-ASA 4-Acetamidosalicylic acid; 4-Cl-SA = 4-chlorosalicylic acid; 5-F$_x$-SA = diflunisal; and SSA = salicylsalicylic acid.

Polymerization.

In one embodiment, the diacids prepared in examples 1-8 were converted to di-anhydrides according to the method described in Conix, Macromol. Synth., 2, 95-99 (1996). In this method, the dicarboxylic acids were acetylated using an excess of acetic anhydride at reflux temperature. The acetic acid and excess acetic anhydride were removed via distillation. No additional purification was required. In a second embodiment of the invention, the dianhydrides were purified and isolated.

A small scale (<1 g), dynamic polymerization vessel is illustrated in FIG. 1. The vessel is constructed from 14/10 jointed microscale glassware components. A cylindrical bottom vial (10 ml) is equipped with a vacuum adaptor; the included O-rings and screw-top joints ensure a vacuum seal, and create a modular system. The stirring shaft is constructed by shaving the edges of the spoon end of a stainless steel lab spoon-spatula (9") to fit through the 14/10 joint of the vial. The spatula end is left flat, which allows the shaft to interlock with the stirring motor. The joint and O-ring at the top of the vacuum adapter form a vacuum-tight fit around the shaft.

A medium scale (1 g-100 g), dynamic polymerization vessel is illustrated in FIG. 2. The polymerization apparatus is constructed with 24/40 joints on 125-250 ml two-necked round-bottom flask. In one neck, a vacuum joint is installed while the other neck holds a Teflon vacuum-stirring adaptor. The stirrer assembly consists of a glass stirring shaft and Teflon paddle (19 mm×48 mm).

Following to the procedure described above, in the embodiment of the invention wherein the dianhydride prepolymers were not isolated, the monomers incorporating the active agents prepared in examples 1-6 were polymerized follows:

The di-anhydrides (500 mg) were heated, in one of the vessels described above, using a silicone oil bath at about 180° C. under high vacuum (<2 mmHg) for 30 min to 12 hours. During this time the melt was actively stirred at about 80 rpm using an overhead stirrer. Polymerization was complete when the viscosity of the melt would plateau and/or the melt would solidify. The polymer was cooled to room temperature, dissolved in a minimal volume of methylene chloride (15 ml), and precipitated into a 20-fold excess of diethyl ether (300 ml). The results of the dymamic polymerization and the polymer properties are summarized in Table 2, and compared to the results for static polymerization.

Example 9

Dynamic Polymerizaiton of 1,10-bis-Salicylic-sebacate

The precursor/monomer prepared in Example 1 was acetylated and polymerized according to the procedure described above. Yield: quantitative. (pale tan solid).

$^1$H-NMR (DMSO-$d_6$): δ 8.20 (d, 2H, ArH), 7.95 (t, 2H, ArH), 7.75 (t, 2H, ArH), 7.40 (d, 2H, ArH), 2.20 (t, 4H, $CH_2$), 1.55 (m, 4H, $CH_2$), 1.25 (b, 8H, $CH_2$). IR (NaCl, cm$^{-1}$): 1792, 1740 (C=O, anhydride), 1760 (C=O, ester). $T_g$=27° C.; $M_w$=29,500; $M_n$=24,600; PDI=1.2

Comparative Example 9C

Figure 3:
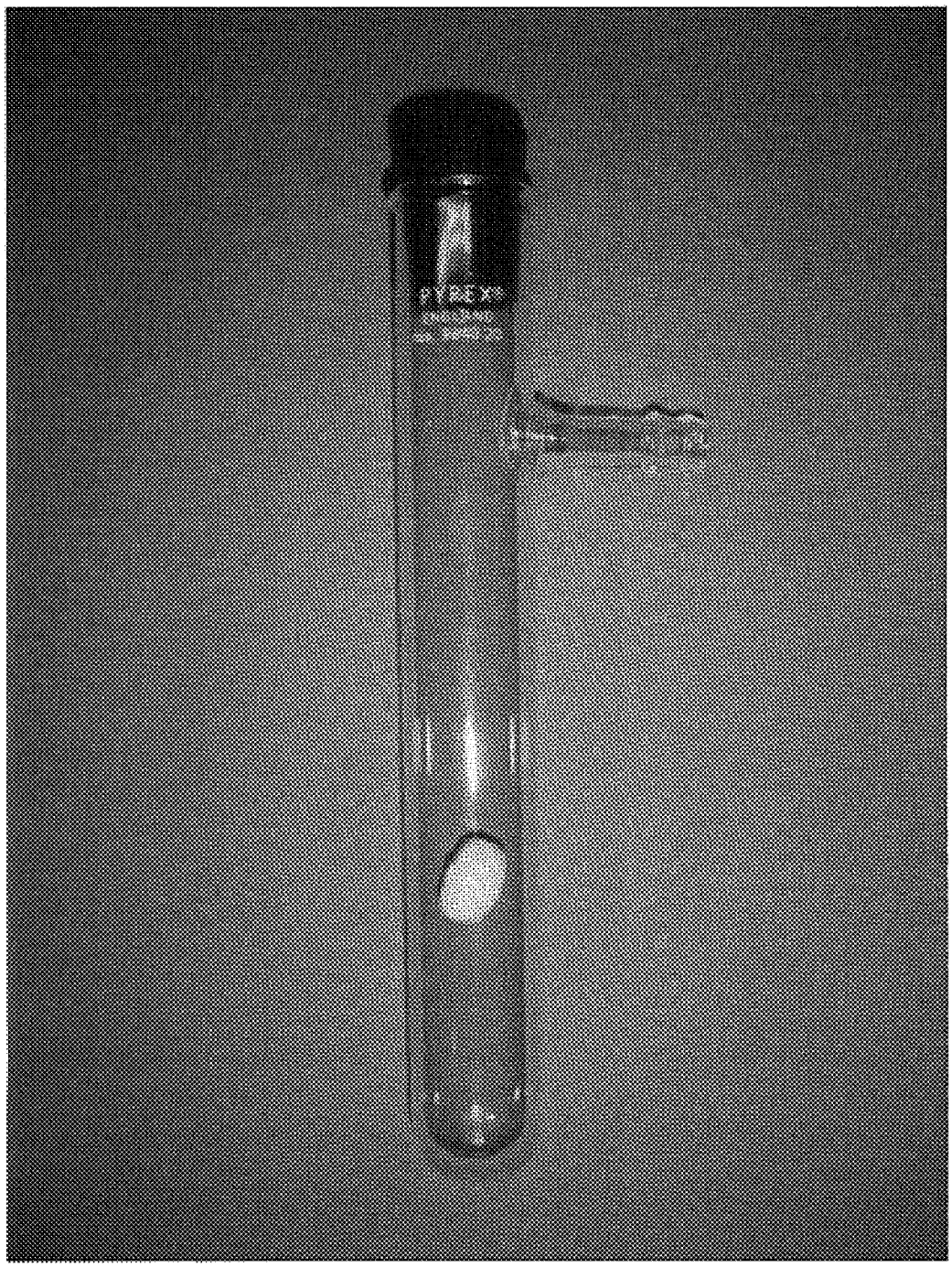
FIG. 3 is a side-arm test tube, containing a magnetic stir bar, useful for polymerization by melt condensation while maintaining high vacuum.

Static Polymerization of 1,10-bis-salicylic-sebacate 1,10-Bis-salicylic-sebacate prepared in Example 1 was acetylated and polymerized using melt condensation polymerization using a side-arm test tube containing a magnetic stir bar, attached to a gas-vacuum manifold (magnetic stirring, at 180° C. under vacuum; <2 mm Hg, FIG. 3) until the monomer solidified. The reaction vessel was flushed with dry nitrogen every 15 min. The product was isolated by methods well known in the art. Yield: quantitative.

Infrared absorption frequencies were 1799, 1793 and 1747 cm$^{-1}$. $T_g$=23° C.; $M_w$=8,000; $M_n$=5,700; PDI=1.4.

Example 10

Dynamic Polymerization Preparation of 5-Chlorosalicylic Polymer (5-Cl-SA)

The precursor/monomer prepared in Example 4 was acetylated and polymerized according to the procedure described above. Yield: quantitative. (pale tan solid).

Infrared absorption frequencies were 1812, 1754, 1703 and 1100 cm$^{-1}$ NMR chemical shifts (DMSO, ppm) δ 7.9 (broad, Ar H, 2 H), 7.7 (broad, Ar H, 2 H), 7.25 (broad, Ar H, 2 H), 2.55 (broad, α-$CH_2$, 4 H), 1.6 (broad, β-$CH_2$, 4 H), and 1.35 (broad, γ-$CH_2$, 4 H). $T_g$=26° C.; $M_w$=5300; $M_n$=4000; PDI=1.3.

Example 11

Dynamic Polymerization Preparation of Diflunisal Polymer (DF)

The precursor/monomer prepared in Example 5 was acetylated and polymerized according to the procedure described above. Yield: quantitative. (pale tan solid).

Infrared absorption frequencies were 1800, 1750, 1704, 1200 and 1142 cm$^{-1}$. NMR chemical shifts (CDCl$_3$, ppm) δ 8.25 (broad, Ar H, 2 H), 7.65 (broad, Ar H, 2 H), 7.4 (broad, Ar H, 2 H), 7.2 (broad, Ar H, 2 H), 6.95 (broad, Ar H, 4H), 2.65 (broad, α-$CH_2$, 4 H), 1.8 (broad, β-$CH_2$, 4 H), and 1.45 (broad, γ-$CH_2$, 4 H). $T_g$=57° C.; $M_w$=21,300; $M_n$=17,200; PDI=1.2.

Example 12

Dynamic Polymerization Preparation of Salicylsalicylic Polymer (SSA)

The precursor/monomer prepared in Example 6 was acetylated and acetylated and polymerized according to the procedure described above. Yield: quantitative. (pale tan solid).

Infrared absorption frequencies were 1799, 1793 and 1747 cm$^{-1}$. NMR chemical shifts (CDCl$_3$, ppm) δ 8.2 (broad, Ar H, 4H), 7.6 (broad, Ar H, 4 H), 7.45 (broad, Ar H, 4 H), 7.15 (broad, Ar H, 4 H), 2.5 (broad, α-$CH_2$, 4 H), 1.8 (broad, β-$CH_2$. 4 H), and 1.35 (broad, γ-$CH_2$, 4 H). $T_g$=26° C.; $M_w$=23,100; $M_n$=19,300; PDI=1.2.

Examples 13-14

Dynamic Polymerization

Following to the procedures described above, the precursor/monomer incorporating the active agents prepared in Examples 2-3 were acetylated and polymerized as described above. The results of the dynamic polymerization and the polymer properties are provided in Table 2.

In the embodiment of the invention wherein the dianhydride prepolymer is purified and isolated, the monomers containing the active agent, e.g., prepared in Example 8, was polymerized as follows:

The purified dianhydrides were heated in one of the vessels described above, using a silicone oil bath at about 110-180° C. under high vacuum (<0.1 mmHg) for about 4 to 24 hours. During this time the melt was actively stirred at about 50 to 80 rpm using an overhead stirrer. Polymerization was complete when the molecular weight of the melt would plateau. The polymer was cooled to room temperature, dissolved in a minimal volume of methylene chloride and precipitated into a 20-fold excess of ethyl ether. The results of the dynamic polymerization and the polymer properties are provided in Table 2.

Example 15

Diflunisal Polymer

The monomer prepared in Example 8 was polymerized according to the procedure described above. The monomer was stirred at 60 rpm at 140° C. for 8 hours yield: 40-60%. (Pale tan solid). $M_w$=33100, $M_n$=18600, PDI=1.78. $T_g$=360° C.

Example 16

Diflunisal Polymer

The monomer prepared in Example 8 was polymerized according to the procedure described above. The monomer was stirred at 60 rpm at 160° C. for 18 h. Yield: 40-60%. (Pale tan solid). $M_w$=142800, $M_n$=48444, PDI=2.95. $T_g$=43.6° C.

TABLE 2

| Ex # | Active Agent[1] | Static Polymerization | | | | Dynamic Polymerization | | | |
|---|---|---|---|---|---|---|---|---|---|
| | | $M_w$ | $M_n$ | PDI | $T_g$ (° C.) | $M_w$ | $M_n$ | PDI | $T_g$ (° C.) |
| 10 | SA | 8,000 | 5,700 | 1.4 | 23 | 29,500 | 24,600 | 1.2 | 27 |
| 11 | 5-Cl-SA | — | — | — | — | 5300 | 4000 | 1.3 | 26.5 |
| 12 | 5-$F_x$-SA | — | — | — | — | 21,300 | 17,300 | 1.2 | 57 |
| 13 | SSA | — | — | — | — | 23,100 | 19,300 | 1.2 | 27 |
| 14 | 4-ASA | — | — | — | — | N/A | 7,900* | N/A | N/A |
| 15 | 5-ASA | — | — | — | — | 8,200 | 5,900 | 1.4 | 26 |
| 16 | 5-$F_x$-SA | — | — | — | — | 33,100 | 18,600 | 1.78 | 36 |
| 17 | 5-$F_x$-SA | — | — | — | — | 142,80 | 48,444 | 2.95 | 43.6 |

[1]SA = Salicylic acid; 5-ASA = 5-Acetamidosalicylic acid; 4-ASA = 4-Acetamidosalicylic acid; 4-Cl-SA = 4-chlorosalicylic acid; 5-$F_x$-SA = diflunisal; and SSA = salicylsalicylic acid.

Example 18

Thermoanalysis of Polymers

The polymers prepared in Examples 16 and 17 were evaluated for their mechanical properties by dynamic mechanical analysis. Samples of each polymer first were pressed into 0.8 mm-thick films using a Carver press operated at 120° F. and 1.2-1.5×10$^4$ psi. These films then were cut into strips approximately 3-4 mm in width and 5-10 mm in length. Strips were mounted into the grips of a DMA 7e (Perkin-Elmer, Bridgeport, Conn.) and extended at a constant load rate of 500 mN/min until either the strip fractured, the maximum extension provided by the instrument was achieved, or the maximum load obtainable with the instrument was delivered. Analysis was conducted at an ambient temperature of 20-25° C. and under helium. Tensile modulus was measured as the initial slope of the stress-strain plot at 1% strain. Ultimate stress and strain were measured as the stress and strain, respectively, at which the strip fractured. For films for which failure was not observed lower limits for ultimate stress, ultimate strain, and toughness were reported. Two strips were evaluated for each polymer. The thermoanalysis of the polymers of 5-$F_x$-SA as a Function of Molecular Weight at 25° C. is summarized in Table 3.

TABLE 3

| | Molecular Weight ($M_w$) | |
|---|---|---|
| Property | 33,000 | 100,000 |
| Tensile Modulus (kPa) | 3500 | 810 |
| Ultimate Stress (kPa) | >2800 | >2600 |
| Ultimate Elongation (%) | >4 | >500 |

Example 17

Hardness of Polymers

The polymers prepared in Examples 14 and 15 also were evaluated for their hardness as a coating. Each polymer first was dissolved in anhydrous chloroform. This solution was applied to a 316 L stainless steel coupon with a knife-edge slider and then dried under vacuum at 40° C. overnight. The hardness of these coatings was determined using the industry-standard ASTM procedure D 3363, "Standard Test Method for Film Hardness by Pencil Test," as commonly practiced by those skilled in the art. In this test pencil with calibrated hardness are applied reproducibly to a coating and hardness measured on a relative scale of increasing hardness as 9B-8B-7B-6B-5B-4B-3B-2B-B-HB-F-H-2H-3H-4H-5H-6H-7H-8H-9H as the softest pencil for which a scratch in the coating is observed. Coatings were evaluated either at ambient temperatures prior to soaking in a solution of phosphate-buffered saline (PBS), after soaking for 5 minutes in PBS incubated at 37° C., or after soaking in this solution for one hour. Soaked coating were blotted dry before application of pencils.

Table 4 presents data for the observed hardness of coatings of two polymers of 5-$F_x$-SA with weight-averaged molecular weight, $M_w$, of approximately 33,000 and 100,000. These data demonstrate that increasing the molecular weight of the polyanhydrides of the invention results in a harder coating. The ability to tailor the hardness of a polymer coating by changing molecular weight is useful for creating coatings that better withstand the stresses associated with usage as an implantable medical device.

TABLE 4

| | Molecular Weight ($M_w$) | |
|---|---|---|
| Condition | 33,000 | 100,000 |
| Before soaking in PBS | F | 3H |
| After 5 minutes in PBS | 2B | B |
| After 60 minutes in PBS | 8B | 4B |

All publications, patents, and patent are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A process for preparing a compound having Formula (I)

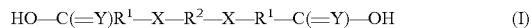

$$HO\text{—}C(\!=\!Y)R^1\text{—}X\text{—}R^2\text{—}X\text{—}R^1\text{—}C(\!=\!Y)\text{—}OH \qquad (I)$$

wherein each $R^1$ is an organic group; each Y is independently O or S; each X is independently an ester linkage, an amide linkage, a thioester linkage or a thioamide linkage; and $R^2$ is a linking group;

comprising reacting a compound of Formula (II)

$$R^3\text{—}R^1\text{—}C(\!=\!O)OH \qquad (II)$$

with a compound of Formula (III)

$$X^2\text{—}C(\!=\!Y)\text{—}R^2\text{—}C(\!=\!Y)\text{—}X^2 \qquad (III)$$

wherein $R^3$ is an hydroxy, amine, or thiol group or an organic radical comprising an hydroxy, amine, or thiol group; and each $X^2$ is a halogen; in the presence of at least 2 equivalents to about 50 equivalents of an organic base; optionally in a suitable solvent.

2. The process of claim 1 wherein each $R^1$ is derived from a compound having Formula (VI):

(VI)

wherein $R^3$ is an hydroxy, amine, or thiol group or an organic radical comprising an hydroxy, amine, or thiol group;

$R^4$ is hydrogen, halo, —$NHR^5$, or aryl optionally substituted with hydroxy, halo or halo$C_{1-4}$alkyl; and $R^5$ is hydrogen, $(C_1\text{-}C_6)$alkyl, $(C_3\text{-}C_6)$cycloalkyl, $(C_3\text{-}C_6)$cycloalkyl$(C_1\text{-}C_6)$alkyl, aryl, heteroaryl, aryl$(C_1\text{-}C_6)$alkyl, or heteroaryl$(C_1\text{-}C_6)$alkyl or —$C(O)C_{1-4}$alkyl.

3. The process of claim 2 wherein $R^4$ is —$NH_2$, —NHAc, —Cl, 2,4-difluoro-phenyl, chloromethyl, difluoromethyl, or —$CF_3$.

4. The process of claim 1 wherein the compound of Formula (II) is salicylic acid, 4-aminosalicylic acid, 5-aminosalicylic acid, 5-chlorosalicylic acid or 5-(2,4-difluorophenyl)salicylic acid.

5. The process of claim 1, wherein each $R_1$ is independently aryl, $(C_{1-8})$alkylene, $(C_{2-8})$alkenylene, heteroaryl, $(C_{3-8})$cycloalkyl, or $(C_{3-8})$cycloalkenyl.

6. The process of claim 2, wherein $R^3$ is —OH, —SH, —$NH_2$, or —$HNR^6$, HO$(C_{1-6})$alkylene; HS$(C_{1-6})$alkylene or $R^6HN(C_{1-6})$alkylene; wherein $R^6$ is hydrogen, $(C_1\text{-}C_6)$alkyl, $(C_3\text{-}C_6)$cycloalkyl, $(C_3\text{-}C_6)$cycloalkyl$(C_3\text{-}C_6)$alkyl, aryl or aryl$(C_1\text{-}C_6)$alkyl.

7. The process of claim 1, wherein $R^3$ is —OH.

8. The process of claim 1, wherein $R^3$ is —$NHR^6$, wherein $R^6$ is hydrogen, $(C_1\text{-}C_6)$alkyl, $(C_3\text{-}C_6)$cycloalkyl, $(C_3\text{-}C_6)$cycloalkyl$(C_1\text{-}C_6)$alkyl, aryl or aryl$(C_1\text{-}C_6)$alkyl.

9. The process of claim 1, wherein $R^3$ is —SH.

10. The process of claim 2, wherein $R^4$ is halo, $NHR^5$, or aryl optionally substituted with hydroxy, halo or halo$C_{1-4}$alkyl; and $R^5$ is hydrogen or —$C(O)C_{1-4}$alkyl.

11. The process of claim 10, wherein $R^4$ is —Cl, or 2,4-difluorophenyl.

12. The process of claim 1, wherein the compound of Formula (II) is salicylic acid, 4-aminosalicylic acid, 5-aminosalicylic acid, 4-(acetylamino)salicylic acid, 5-(acetylamino)salicylic acid, 5-chlorosalicylic acid, salsalate, 4-thiosalicylic acid, 5-thiosalicylic acid, 5-(2,4-difluorophenyl)salicylic acid, diflunisal, 4-trifluoromethylsalicylic acid, sulfasalazine, dichlofenac, penicillamine, balsalazide, olsalazine, mefenamic acid, carbidopa, levodopa, etodolac, cefaclor, or captopril.

13. The process of claim 1, wherein X is independently an amide linkage or an ester linkage.

14. The process of claim 13, wherein one X is an amide linkage, and one X is an ester linkage.

15. The process of claim 13, wherein each X is an amide linkage.

16. The process of claim 13, wherein each X is an ester linkage.

17. The process of claim 1, wherein $R^2$ is a divalent, branched or unbranched, saturated or unsaturated hydrocarbon chain, having from 1 to 25 carbon atoms, wherein one or more of the carbon atoms is optionally replaced by (—O—) or (—NR—), or an amino acid derivative or a peptide, and wherein the chain is optionally substituted on carbon with one or more substituents selected from the group consisting of $(C_1\text{-}C_6)$alkoxy, $(C_3\text{-}C_6)$cycloalkyl, $(C_1\text{-}C_6)$alkanoyl, $(C_1\text{-}C_{12})$alkanoyloxy, $(C_1\text{-}C_6)$alkoxycarbonyl, $(C_1\text{-}C_6)$alkylthio, —OP(=O)O$(C_1\text{-}C_{12})$alkyl, azido, cyano, nitro, halo, hydroxy, oxo, carboxy, aryl, aryloxy, heteroaryl, or heteroaryloxy.

18. The process of claim 1, wherein $R^2$ is a divalent, branched or unbranched, saturated or unsaturated hydrocarbon chain, having from 3 to 20 carbon atoms, wherein one or more of the carbon atoms is optionally replaced by (—O—), (—C(O)O—), (—C(S)O—), (—C(O)$NR^7$—), (—C(S)$NR^7$—), or (—$NR^7$—), wherein $R^7$ is hydrogen or $(C_1\text{-}C_6)$alkyl.

19. The process of claim 18, wherein $R^7$ is hydrogen, methyl, ethyl or propyl.

20. The process of claim 1, wherein $R^2$ is a divalent, branched or unbranched, saturated or unsaturated hydrocarbon chain, having from 3 to 20 carbon atoms.

21. The process of claim 1, wherein $R^2$ is a divalent, branched or unbranched, hydrocarbon chain, having from 4 to 15 carbon atoms.

22. The process of claim 21, wherein the hydrocarbon chain is n-butyl, n-hexyl, n-octyl, n-decyl, n-dodecyl or n-tetradecyl.

23. The process of claim 22, wherein the hydrocarbon chain is n-octyl, or n-tetradecyl.

24. The process of claim 1, wherein $R^2$ is an amino acid derivative.

25. The process of claim 1, wherein $R^2$ is a peptide.

26. The process of claim 1, wherein $R^2$ is —$(CHR^9)_4$— where each $R^9$ is hydrogen, —C(=O)$(CH_2)_{10}CH_3$ or —OP(=O)O$(CH_2)_{10}CH_3$.

* * * * *